United States Patent
Amoros et al.

(10) Patent No.: US 7,384,518 B2
(45) Date of Patent: Jun. 10, 2008

(54) METHOD FOR PURIFYING LACTAMS

(75) Inventors: Daniel Amoros, Venissieux (FR);
Philippe Leconte, Meyzieu (FR);
Pierre Coqueret, Francheville (FR)

(73) Assignee: Rhodia Polyamide Intermediates, Saint Fons (FR)

( * ) Notice: Subject to any disclaimer, the term of this patent is extended or adjusted under 35 U.S.C. 154(b) by 17 days.

(21) Appl. No.: 10/296,512

(22) PCT Filed: May 28, 2001

(86) PCT No.: PCT/FR01/01644
§ 371 (c)(1),
(2), (4) Date: Jul. 30, 2003

(87) PCT Pub. No.: WO01/90065
PCT Pub. Date: Nov. 29, 2001

(65) Prior Publication Data
US 2004/0014965 A1    Jan. 22, 2004

(51) Int. Cl.
*B01D 3/34*   (2006.01)
*C07D 201/08* (2006.01)
*C07D 201/16* (2006.01)

(52) U.S. Cl. .................. 203/14; 203/35; 203/37; 203/72; 203/78; 540/538; 540/540

(58) Field of Classification Search .............. 203/14, 203/34, 36, 37, 48, 35, 72, 78; 540/538, 540/540
See application file for complete search history.

(56) References Cited

U.S. PATENT DOCUMENTS

| | | | |
|---|---|---|---|
| 4,301,073 A | | 11/1981 | Fuchs et al. |
| 4,341,709 A | * | 7/1982 | Hofen et al. ............ 549/272 |
| 4,457,807 A | * | 7/1984 | Rulkens et al. ........... 203/72 |
| 4,720,328 A | * | 1/1988 | Corbin et al. ............. 203/37 |
| 4,892,624 A | | 1/1990 | Fuchs et al. |
| 5,136,052 A | | 8/1992 | Van Geysel et al. |
| 5,241,066 A | * | 8/1993 | Davis et al. ............ 540/540 |
| 5,458,740 A | * | 10/1995 | Losier et al. ............ 203/34 |

(Continued)

FOREIGN PATENT DOCUMENTS

DE        81 846        5/1971

(Continued)

*Primary Examiner*—Virginia Manoharan
(74) *Attorney, Agent, or Firm*—Buchanan, Ingersoll & Rooney, PC

(57) ABSTRACT

A method and a plant are disclosed for purifying lactams, particularly lactams obtained by cyclizing hydrolysis of aminonitrile. The purification of ε-caprolactam obtained by cyclizing hydrolysis of aminocapronitrile is described which includes eliminating the ammonia from the reaction medium of the hydrolysis, then recovering the lactam from said medium in purified form. The recovery is carried out by performing at least a distillation of the lactam in the presence of a base producing optionally a fronts fraction comprising compounds more volatile than the lactam, a fraction comprising the lactam to be recovered to the degree of desired purity and a distillation tails comprising the lactam and compounds less volatile than the lactam. The distillation tails are treated by various processes such as evaporation in thin layers to recover the major part of the caprolactam and recycling the latter in the purification process. The method and plant enables a high rate of recovery of the caprolactam contained in the hydrolysis medium, while observing required criteria of purity.

18 Claims, 2 Drawing Sheets

U.S. PATENT DOCUMENTS

Figure 1:
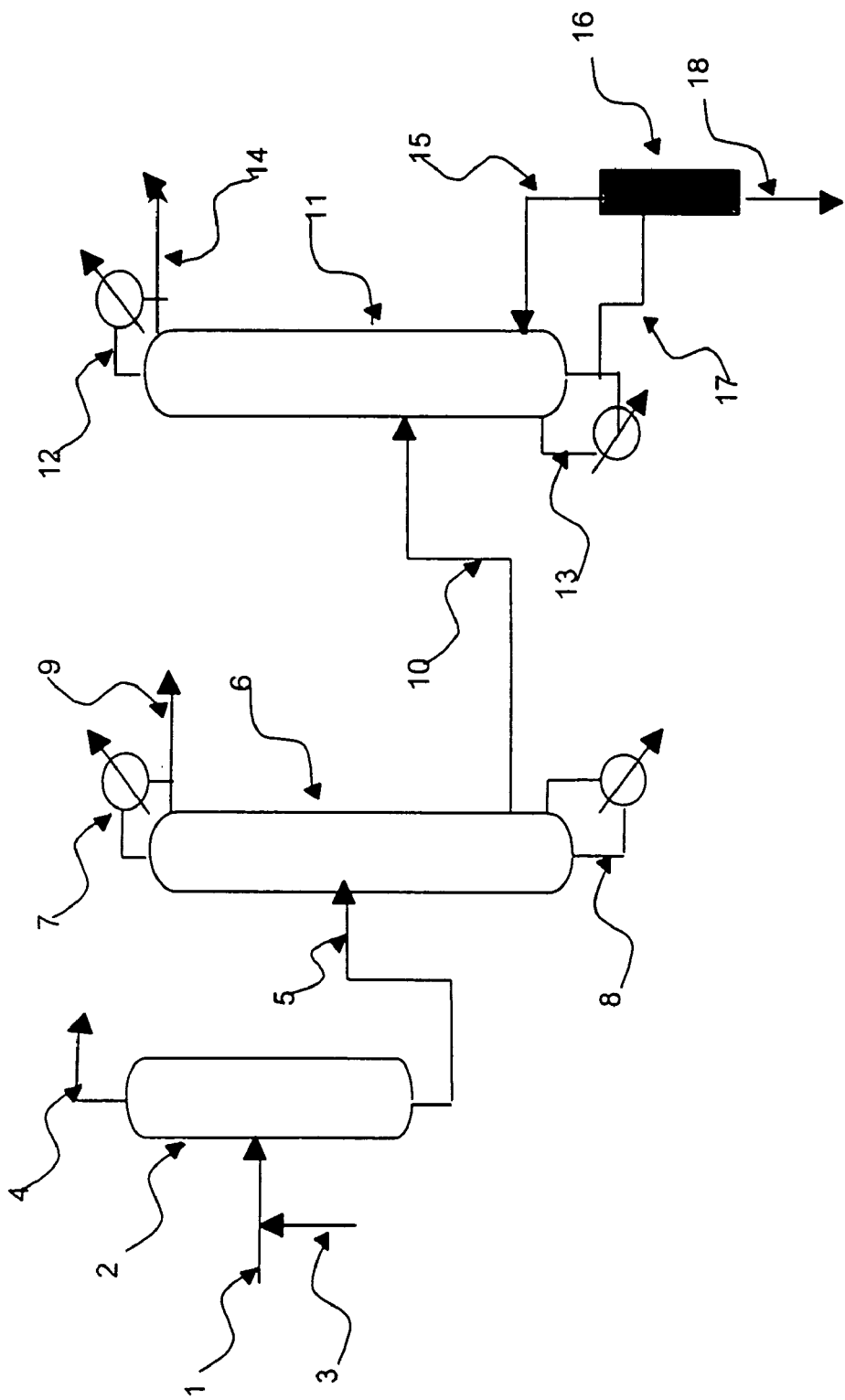

| | | | |
|---|---|---|---|
| 5,496,941 A | * | 3/1996 | Ritz et al. .................. 540/540 |
| 5,700,358 A | * | 12/1997 | Fuchs et al. .................. 203/31 |
| 6,187,917 B1 | * | 2/2001 | Mayer et al. ................ 540/540 |
| 6,635,151 B1 | * | 10/2003 | Bocquenet et al. ........... 203/14 |
| 6,972,075 B2 | * | 12/2005 | Luyken et al. ................ 203/75 |

FOREIGN PATENT DOCUMENTS

| | | |
|---|---|---|
| DE | 31 06 350 | 12/1981 |
| DE | 152 914 | 12/1981 |
| DE | 226 560 | 8/1985 |
| DE | 226 561 | 8/1985 |
| DE | 226 562 | 8/1985 |
| DE | 267 729 | 5/1989 |
| DE | 195 48 289 | 6/1997 |
| EP | 0 306 874 | 3/1989 |
| WO | WO 98/05636 | 2/1998 |

* cited by examiner

METHOD FOR PURIFYING LACTAMS

The present invention relates to a process for the purification of lactams, more particularly of lactams obtained by the cyclizing hydrolysis of aminonitrile.

The invention relates more particularly to the purification of ε-caprolactam obtained by the cyclizing hydrolysis of aminocapronitrile.

Several processes for the synthesis of ε-caprolactam, a major chemical intermediate used in particular in the production of polyamides and more particularly of polyamide-6, have been provided. One of the most widely used processes industrially consists of a Beckmann rearrangement of cyclohexanone oxime in the presence of sulphuric acid or of oleum.

Another process which forms the subject-matter of numerous studies consists in obtaining ε-caprolactam by the cyclizing hydrolysis of aminocapronitrile. This reaction, disclosed in French Patent 2 029 540, can be carried out in the liquid phase in the presence of solvents and of catalysts or, as disclosed in U.S. Pat. No. 2,357,484, in the gas phase with alumina as catalyst.

Patent EP 150 295 also relates to a process for the cyclizing hydrolysis of aminocapronitrile in the gas phase in the presence of a catalyst based on copper and on vanadium.

The ε-caprolactam obtained by these synthetic processes has to be purified in order to obtain a chemical intermediate or a monomer which makes it possible in particular to manufacture polymers exhibiting characteristics satisfactory for the manufacture of finished products, such as yarns, fibres, and the like.

Numerous purification processes have been provided for the treatment of the caprolactam obtained by the Beckmann rearrangement of cyclohexanone oxime.

Processes for the purification of the caprolactam obtained by the cyclizing hydrolysis of aminocapronitrile have also been provided. Thus, U.S. Pat. No. 5,496,941 discloses a process which consists in separating the products with low boiling points and the products with high boiling points from the hydrolysis reaction medium. This separation is obtained in particular by distillation of the caprolactam.

The caprolactam thus recovered is subjected to a hydrogenation, then either to a treatment through ion-exchange resins or to a distillation in the presence of sulphuric acid, and, finally, to a distillation in the presence of a base.

Other purification processes have been provided. Thus, Patent WO 98/05636 provides a process for the purification by liquid/liquid extraction using a solvent with an acidic nature or by a treatment through resins.

In these processes, a final distillation of the caprolactam is generally provided in order to obtain a product which satisfies the criteria of purity required, in particular for its use as monomer in the manufacture of polyamides, such as polyamide-6.

However, this final distillation results in a high loss of caprolactam, which is very harmful to the general economics of the process.

Thus, in the case of the purification of a caprolactam obtained by the Beckmann rearrangement reaction, U.S. Pat. No. 4,301,073 provides a process for purifying the caprolactam which comprises a stage of extraction by a solvent and then a distillation in a basic medium. The distillation residue is treated to recover as much as possible of the caprolactam. This treatment consists of further distillations and a treatment with a strong acid of the caprolactam thus distilled before it is recycled in the extraction stage. This process makes it possible to improve the degree of recovery of the caprolactam but requires the use of an acid for the treatment before recycling. This recycling process is complex and requires a significant investment in order to carry out the acid treatment. Furthermore, this process cannot be transposed to the treatment of a caprolactam synthesized by a novel reaction, which can generate entirely different impurities requiring novel purification processes.

One of the aims of the present invention is to overcome these disadvantages by providing a process and a plant for the purification of a lactam resulting from the cyclizing hydrolysis of an aminonitrile which make it possible to obtain a high degree of recovery of lactam of high purity.

To this end, the invention provides a process for the purification of lactam, more particularly of ε-caprolactam, obtained by the cyclizing hydrolysis of an aminonitrile, more particularly of aminocapronitrile, which consists in removing the ammonia from the hydrolysis reaction medium and in then recovering the lactam from the said medium in the purified form.

According to the invention, this recovery is carried out by employing at least one distillation of the lactam in the presence of a base, optionally producing a top fraction comprising compounds which are more volatile than the lactam, a fraction comprising the lactam to be recovered with the desired degree of purity and a distillation bottom product comprising lactam and compounds which are less volatile than the lactam.

Thus, the distillation bottom product or residue recovered in the stage of purification by distillation predominantly comprises lactam, the impurities being composed mainly of salts and of reaction by-products.

This distillation bottom product is subjected, according to the invention, to a treatment which consists in separating most of the lactam present in the distillation bottom product and in recycling the said separated lactam in any stage of the purification process or in the medium obtained after the cyclizing hydrolysis.

According to the invention, this treatment of the distillation bottom product consists either of a recovery of the lactam by, for example, thin-layer evaporation of the lactam or crystallization of the latter or of a separation of the lactam from the other impurities, for example by extraction of most of the impurities with water.

The crystallization of the lactam can be carried out according to conventional crystallization processes with, as solvent, either water or an aqueous solution saturated with lactam or the lactam itself. It is advantageously carried out in a single stage. However, if necessary, two or more crystallization stages can be employed.

A crystallization process and the conditions for its implementation are disclosed, for example, in Patents EP 943 608 and U.S. Pat. No. 4,882,430.

The lactam thus obtained is recycled in the device for distillation in a basic medium, either by direct feeding to the distillation column at a predetermined level or by addition to the stream of reaction medium entering the said column, or at another stage of the process for the purification and recovery of the lactam or even in the medium resulting from the cyclizing hydrolysis.

According to a second embodiment of the invention, the distillation bottom product is treated in a thin-film or thin-layer evaporation process. The vaporized lactam is recycled in the distillation device under conditions similar to those of the embodiment employing the crystallization. The evaporation of the lactam is obtained by heating at a temperature between 130° C. and 150° C. under a pressure of less than 10 mbar.

Finally, in a third embodiment, the distillation bottom product can be treated with water to dissolve the impurities, in particular the salts, the lactam recovered after separation by settling advantageously being recycled in the process for the purification of the lactam by distillation in an acidic medium and then in a basic medium.

These processes for the treatment of the distillation bottom product make it possible to recover at least 90% by weight, advantageously at least 95%, of the lactam present in the said bottom product. The losses of lactam in the purification process are thus restricted to less than 3% by weight of the participating lactam.

The process of the invention thus makes it possible to restrict the losses of lactam to a very low level during the purification by basic distillation. These losses have only a very slight affect on the economics of the process and in particular the quality of the lactam recovered is of a very high level.

According to the invention, the medium comprising the lactam to be recovered can be the reaction medium for the cyclizing hydrolysis of aminonitrile after evaporation of the ammonia. The said reaction medium could be subjected to a hydrogenation before the evaporation of the ammonia.

This reaction medium, participating in the basic distillation, may have been subjected to several preliminary treatments after evaporation of the ammonia.

In an embodiment of the invention, the hydrolysis reaction medium is treated to remove the products which are respectively less volatile and more volatile than the lactam. This treatment, disclosed in U.S. Pat. No. 5,496,941, consists in evaporating the ammonia, the water and the other volatile products and in then distilling the lactam. The hydrolysis reaction medium treated by the basic distillation of the present invention will thus be the lactam recovered by distillation.

In another embodiment, in particular when the cyclizing hydrolysis is carried out in the vapour phase, only the ammonia is extracted from the reaction medium, which may or may not have been subjected to a hydrogenation prior to the removal of the ammonia.

The lactam recovered by distillation or a ammonia-free reaction medium can be subjected to a hydrogenation or an oxidizing treatment, for example, before being fed to the basic distillation.

In another embodiment, the process for the purification of the lactam can comprise a treatment through an ion-exchange resin in an acidic medium or a distillation in the presence of a strong acid, for example sulphuric acid.

The process for the purification and recovery of the lactam can also comprise one or more successive crystallizations of the lactam, the lactam thus crystallized forming the medium fed to the basic distillation in accordance with the invention.

Consequently, the distillation process in accordance with the invention is a stage in a lactam purification process which can be combined with numerous other known treatments of lactams used in the numerous disclosed purification processes.

According to another characteristic of the invention, the purification process of the invention can be employed in a distillation process comprising several distillation columns mounted in series in order to carry out the successive separation of the various products.

These plants for the implementation of the purification process by distillation in a basic medium or an acidic medium and then a basic medium are also subject-matters of the present invention.

In a first embodiment in accordance with the invention which is suitable for carrying out the treatment in a basic medium of the lactam to be purified, the plant comprises a first distillation column to which the lactam to be purified is fed with a predetermined amount of base. In this column, known as the dehydration column, the water is removed in the form of a top fraction, the distillation bottom product, comprising the lactam and the base, being fed to a second distillation column.

In this second distillation column, the products which are more volatile than the lactam are removed in the form of a top fraction and the separated lactam is fed to a third distillation column.

In this third column, the lactam is distilled and recovered as a top fraction, and the distillation bottom product can advantageously be treated according to the processes of the invention in order to recover most of the lactam. The lactam recovered from the distillation bottom product is advantageously recycled in the second distillation column.

According to a second embodiment in accordance with the invention, the plant also comprises three distillation columns mounted in series. The first column is, as in the first embodiment, a dehydration column which makes it possible to remove most, preferably all, of the water.

In the second column, the least volatile compounds, and in particular less volatile than the lactam, are separated and constitute a distillation bottom product, and the lactam recovered at the column top is fed to the third column.

In this final column, the purified lactam is collected in the form, advantageously, of an intermediate fraction by withdrawal, either in the vapour phase or in the liquid phase. The top fraction, composed of the compounds which are more volatile than the lactam, is removed and the distillation bottom product is preferably recycled in the second column.

In this embodiment, the distillation bottom product from the second column is advantageously treated in order to recover the lactam according to the process of the invention. The lactam thus recovered is advantageously recycled in the second column.

Preferably, the basic compound is added to the medium to be treated before it is fed to the first dehydration stage.

However, the invention also relates to a process which consists in treating the medium comprising the lactam to be purified by distillation in an acidic medium and more particularly in sulphuric acid medium, followed by distillation in a basic medium. Such a treatment is, according to the invention, employed in a plant in accordance with the second embodiment described above.

In this second embodiment, the acid is added to the medium to be treated before it is fed to the dehydration column, the base being added to the top fraction produced in the second distillation column before it is fed to the third distillation column.

The salts generated by the presence of the acid, for example amine sulphates or sulphates originating from the neutralization of the base, are removed and bled off in the distillation bottom product produced in the second distillation column. This distillation bottom product is advantageously subjected to a lactam recovery treatment which, in the present case, can advantageously be:

either a washing of the distillation bottom product with water to dissolve the salts, such as ammonium and/or amine sulphates, the organic phase, after separation of the aqueous phase and the organic phase composed of the lactam, preferably being recycled in the medium fed to the dehydration column or recycled in the second column, or alternatively subjected to another treatment, such as thin-layer evaporation or crystallization, or an evaporation of the lactam carried out in a thin-film or thin-layer evaporator, or a crystallization of the lactam from water, an aqueous lactam solution or lactam.

These treatments can be combined, in particular the washing with water can be carried out prior to the evaporation or the crystallization.

According to a characteristic of the invention, the lactam is advantageously ε-caprolactam obtained by the cyclizing hydrolysis of aminocapronitrile either in the vapour phase or in the liquid phase, with or without solvent.

The aminonitrile is, for example, produced by partial hydrogenation of adiponitrile. This reaction is disclosed in particular in U.S. Pat. No. 4,601,859, U.S. Pat. No. 2,762,835, U.S. Pat. No. 2,208,598, DE 4 235 466 and U.S. Pat. No. 5,981,790.

The ammonia present in the cyclizing hydrolysis reaction medium is removed by distillation or flashing.

The reaction medium fed in the process of the invention can comprise at least 99.9% by weight of lactam. This concentration range is given only by way of indication. Thus, media comprising less lactam can also be purified by the process of the invention.

By way of nonlimiting indication, the operating conditions of the various columns of the second embodiment of the plant according to the invention are given below.

The first dehydration stage is carried out at a temperature of between 100° C. and 130° C. approximately at a pressure of between 50 mbar and 200 mbar approximately.

The dehydrated fraction is fed to a second distillation column in which the second stage of separation of the products with high boiling point is carried out by production of a distillation bottom product.

The operating conditions of this column are a column bottom temperature of less than 150° C. and a pressure of between 5 and 10 mbar.

The top fraction thus produced comprises less than 100 ppm of impurities with a higher boiling point than the lactam.

This top fraction is fed to a further distillation column, the operating conditions of which are a column bottom temperature of less than 150° C. and a pressure of between 5 and 10 mbar.

The lactam, in particular ε-caprolactam, produced as intermediate fraction exhibits a degree of purity which satisfies the criteria required for polyamide manufacture, in particular for textile applications. Preferably, this intermediate fraction is withdrawn in the vapour phase from the column in order to obtain a very low concentration of products with a high boiling point. However, it is also possible to withdraw this intermediate fraction in the liquid phase, without departing from the scope of the invention.

The distillation bottom product obtained in the column bottom is recycled, in an embodiment of the invention, in the second distillation column.

In a preferred embodiment of the invention in accordance with the process for the purification of the lactam of the invention, the distillation bottom product collected in the second column bottom is fed to a stage for separation of the lactam, for example a thin-film or thin-layer evaporation process at a temperature of less than 150° C. and under a pressure of between 5 and 10 mbar.

In another preferred embodiment of the invention, this distillation bottom product is subjected to a crystallization process in order to recover the lactam, more particularly caprolactam.

It is also possible to treat this distillation bottom product with water in order to extract the salts, more particularly the sulphates, originating from the neutralization of the free bases present in the hydrolysis medium. The organic phase recovered, comprising the lactam, is either recycled in the dehydration column or the second column, or subjected to a further stage of separation of the lactam, such as a thin-film or thin-layer evaporation or a crystallization.

According to the invention, a base chosen from the group consisting of alkali metal hydroxides, alkaline earth metal hydroxides and metal carbonates, for example sodium hydroxide, lithium hydroxide, potassium hydroxide, magnesium hydroxide, calcium hydroxide, sodium carbonate, magnesium carbonate, lithium carbonate or mixed carbonates, can be used as basic compound. Preferably, an aqueous sodium hydroxide solution is used. The amount of base added can vary within wide limits. Advantageously, it is between 0.05 and 2 g of base per 1 kg of caprolactam or lactam.

As indicated above, this base is added either to the medium to be treated fed to the dehydration stage or to the top fraction resulting from the second column of the second embodiment of the plant, before it is fed to the third column.

According to the invention, it is also possible to add an acid, preferably sulphuric acid, to the medium fed to the dehydration stage. The amount of acid added is determined as a function of the amount of free bases present in the medium to be treated. This amount of free bases is determined by potentiometric titration of the medium. The amount of acid added is between 0.5 mol of acid per mole of free bases and one mole of acid per mole of free bases, preferably between 0.7 and 0.9 mol of acid per mole of free bases. This concentration range makes it possible to obtain meltable salts and a weak corrosive action of the medium.

Figure 2:
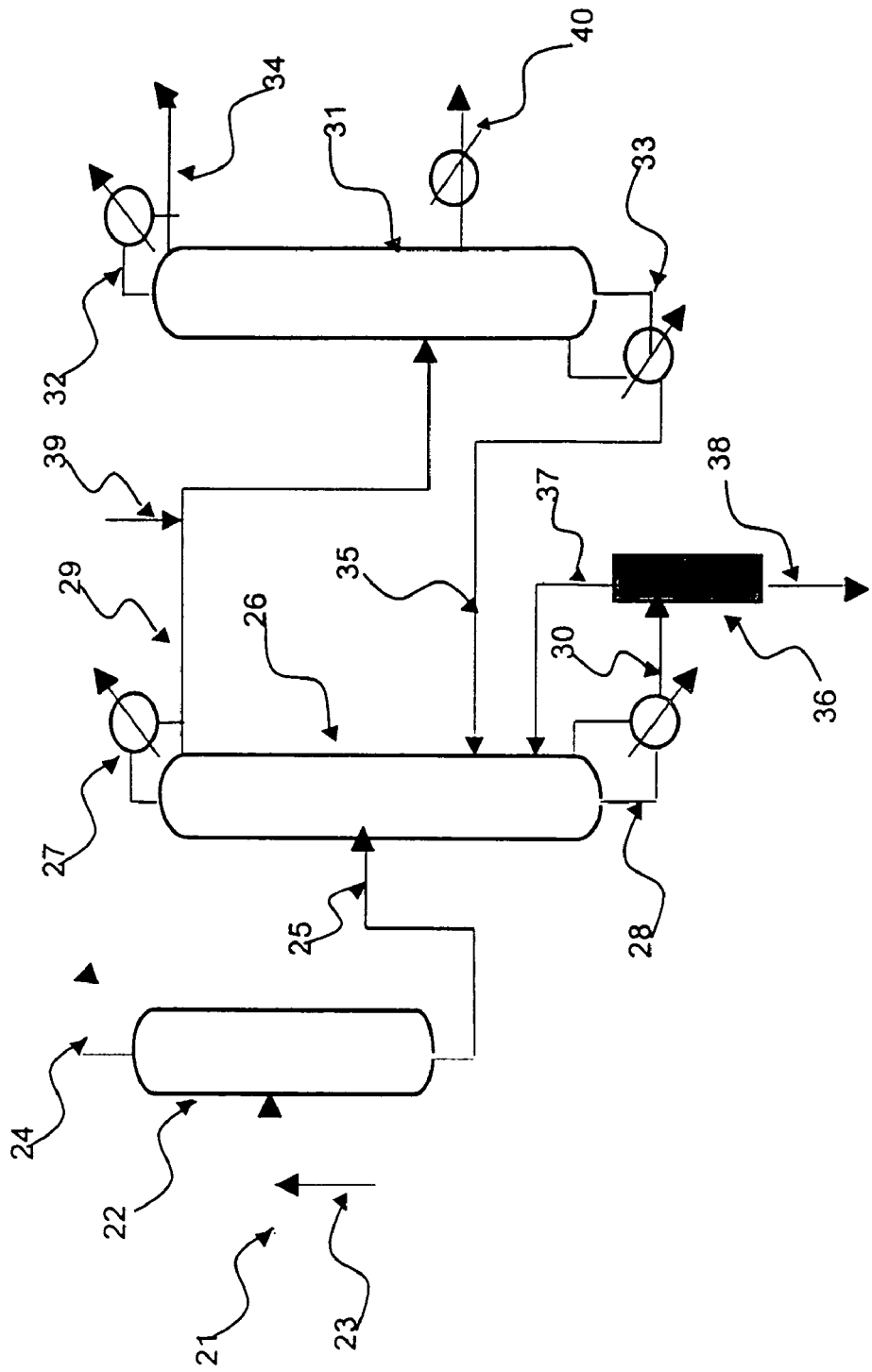

Other advantages and details of the invention will become more clearly apparent in the light of the detailed description of examples, made with reference to the appended figures, in which:

FIG. 1 represents a block diagram of a first embodiment of the plant of the invention, and FIG. 2 represents a block diagram of a second embodiment of the plant of the invention.

EXAMPLE 1

A medium resulting from the cyclizing hydrolysis of an aminocapronitrile obtained by hemihydrogenation of adiponitrile was treated by hydrogenation before distillation (stripping) of the ammonia. The resulting medium was treated by passing through an ion-exchange resin. The conditions for carrying out these treatments are disclosed in the abovementioned patents or patent applications and in particular in Patent Applications WO 98/05636 and FR 2 786 180.

This medium comprises approximately 65% by weight of caprolactam and exhibits the following purity characteristics Permanganate number ($PN_{MnO_4}$): 35

Content of volatile bases ($N_{VB}$): 1.8 meq/kg

UV number ($N_{UV}$): 0.5

These characteristics are determined according to standardized procedures disclosed in Standard ISO 8660 for the permanganate number ($PN_{MnO_4}$), Standard ISO 8661 for the content of volatile bases ($N_{VB}$) and Standard ISO 7059 for the UV number ($N_{UV}$). With reference to FIG. 1, this medium is, in accordance with the invention, fed via the pipe 1 to the first distillation column 2, after addition, via the pipe 3, of 0.6 g of pure sodium hydroxide, in the form of a concentrated solution, per kg of caprolactam.

The column 2 has a bottom temperature of less than 130° C. and a pressure of 70 mbar.

The top fraction 4 is composed of water.

The distillation bottom product 5 comprises an amount of water of less than 0.5% by weight.

This distillation bottom product 5 is fed to a second column 6 operating under reflux 7, 8.

The top fraction 9, composed essentially of caprolactam and of compounds with a lower boiling point than that of caprolactam, is removed. The amount of caprolactam removed represents 0.5% by weight of the caprolactam fed in. The distillation bottom product 10, comprising the caprolactam, is fed to a third column 11 also operating under reflux 12, 13.

The top fraction 14 is composed of caprolactam of conformable purity.

The purity characteristics are:
Permanganate number ($PN_{MnO_4}$): 1.5
Content of volatile bases ($N_{VB}$): 0.28 meq/kg
UV number ($N_{UV}$): 0.025

The distillation bottom product 15, composed predominantly of caprolactam and comprising, as impurities, compounds with a higher boiling point than that of caprolactam, is fed to a scraped-film evaporator 16 operating under a pressure of 10 mbar and a temperature of 150° C.

The evaporated caprolactam is recycled via the pipe 17 to the third column 11.

The non-evaporated products are removed via the pipe 18.

The balance by weight of the caprolactam fed to the first column 2 and that produced at the top 14 of the third column 11 shows that 99.1% of the participating caprolactam is recovered with a high and suitable degree of purity.

EXAMPLE 2

An aminocapronitrile hydrolysis medium after distillation (stripping) of the ammonia is treated in a plant in accordance with the invention, represented diagrammatically by FIG. 2, according to a second embodiment of the process for the purification of caprolactam.

The characteristics of this medium are as follows:
Permanganate number ($PN_{MnO_4}$): 381
Content of volatile bases ($N_{VB}$): 232 meq/kg
UV number ($N_{UV}$): 12

Furthermore, the concentration of free bases, determined by potentiometric titration, is equal to 189 meq per kg of medium or solution.

With reference to FIG. 2, this medium is, in accordance with the invention, fed via the pipe 21 to the first distillation column 22, after addition, via the pipe 23, of 0.8 mol of sulphuric acid, in the form of a concentrated solution, per mole of free bases present in the medium to be treated.

The column 22 has a bottom temperature of less than 130° C. and a pressure of 70 mbar.

The top fraction 24 is composed of water.

The distillation bottom product 25 comprises an amount of water of less than 0.5% by weight.

This distillation bottom product 25 is fed to a second column 26 operating under reflux 27, 28.

The top fraction 29 resulting from this second column 26, composed essentially of caprolactam and compounds with a lower boiling point than that of caprolactam, is fed to a third column 31 also operating under reflux 32, 33, after addition, via the pipe 39, to this top fraction of 0.6 g of pure sodium hydroxide, in the form of a concentrated solution, per kg of caprolactam.

The top fraction 34 from the third column 31, composed of compounds with a lower boiling point than that of caprolactam, is removed.

The distillation bottom product 35 is recycled, in the embodiment illustrated, in the second column 26.

The purified caprolactam is drawn off from this third column 31 in the form of an intermediate fraction 40. This withdrawal operation is carried out either in the gaseous form at the lower part of the column or in the liquid form in the upper part of the column.

The characteristics of the caprolactam produced are:
Permanganate number ($PN_{MnO_4}$): 2
Content of volatile bases ($N_{VB}$): 0.25 meq/kg
UV number ($N_{UV}$): 0.03

According to the process of the invention, the distillation bottom product 30 from the second column 26, composed predominantly of caprolactam and comprising, as impurities, compounds with a higher boiling point than that of caprolactam and salts formed by the neutralization of the free bases by the sulphuric acid, is fed to a scraped-film evaporator 36 operating under a pressure of 10 mbar and a temperature of 150° C.

The evaporated caprolactam is recycled, in the embodiment illustrated, via the pipe 37 in the second column 26.

The non-evaporated products are removed via the pipe 38.

The balance by weight of the caprolactam fed to the first column 22 and that produced in the form of an intermediate fraction 40 from the third column 31 shows that 98.9% of the participating caprolactam is recovered with a high and suitable degree of purity.

EXAMPLE 3

Example 2 is repeated, with the difference that the distillation bottom product 30 from the second column is treated by addition of water in order to obtain a solution comprising approximately 80% by weight of caprolactam. The mixture is subjected to stirring. After mixing, two liquid phases are formed. The lower phase is an aqueous phase which comprises 60% by weight of amine sulphates, corresponding to approximately 70% of the amount of amines present in the caprolactam charged to the dehydration column in the purification process. The upper phase, composed essentially of caprolactam, is recycled in the first distillation column.

By this process, 99% of the caprolactam charged in the distillation column is recovered with a high degree of purity, suitable for use of this product in the manufacture of polyamide, in particular for textile applications.

EXAMPLE 4

Example 2 is repeated, with the difference that the distillation bottom product 30 from the second column is treated by a process of crystallization in one stage of the caprolactam.

The distillation bottom product is concentrated under reduced pressure in order to obtain a concentration by weight of water of approximately 8%.

The concentrated solution is at a temperature of 40° C. and is then cooled to a temperature in the region of 20° C. with a rate of cooling of approximately 10° C. per hour.

The crystals formed are recovered by filtration through a sintered glass filter. The aqueous mother liquors recovered are stored for possible recycling.

The solid cake of caprolactam crystals is washed with a saturated aqueous solution of caprolactam. The degree of washing as wet base is advantageously between 1 and 5.

The recovered caprolactam has a sufficient purity to be recycled in the distillation process.

By this process, 99% of the caprolactam charged in the distillation column is recovered with a high degree of purity, suitable for use of this product in the manufacture of polyamide, in particular for textile applications.

The invention claimed is:

1. A plant for the purification of lactams by distillation, comprising:
   three distillation columns mounted in series, the first being a dehydration column, the second column and the third column acting to separate either the compounds which are less volatile than the lactam as a bottom product of either the second or the third column, or the compounds which are more volatile,
   means for adding an acidic compound to the lactam before it is fed to the dehydration column,
   means for adding a basic compound to the lactam before it is fed to the third column, and
   means for withdrawing the purified lactam from the third column, and
   means for recovering the lactam present in the bottom product of either the second or third column containing compounds less volatile than the lactam, and for recycling recovered lactam for distillation.

2. The plant according to claim 1, further comprising:
   means for removing the compounds which are more volatile than the lactam as a top fraction from the second column.

3. The plant according to claim 1, further comprising:
   means for separating the compounds which are less volatile than lactams as distillation bottom product from the third column.

4. The plant according to claim 1, further comprising:
   means for treating the distillation bottom product from the third column,
   means for recovering the lactam present, and
   means for recycling the recovered lactam for distillation.

5. The plant according to claim 4, wherein the means for treating is selected from the group consisting of a means for evaporating by thin-film or thin-layer evaporation, a means for crystallizing, and a means for washing with water.

6. The plant according to claim 1, further comprising:
   means for removing the compounds which are more volatile than the lactam as a top fraction from the third column, and
   means for removing the compounds which are less volatile than the lactam as distillation bottom product from the second column.

7. The plant according to claim 6, further comprising:
   means for treating the distillation bottom product from the second column,
   means for recovering the lactam present, and
   means for recycling the recovered lactam for distillation.

8. The plant according to claim 1, wherein:
   the means for adding a basic compound to the lactam comprises means for adding the basic compound before it is fed to the dehydration column.

9. The plant according to claim 1, wherein the basic compound comprises alkali metal hydroxides.

10. The plant according to claim 1, wherein the amount of the basic compound is between 0.05 g and 2 g per 1 kg of lactam.

11. The plant according to claim 1, wherein the acidic compound is sulphuric acid.

12. The plant according to claim 1, wherein the amount of the acidic compound is between 0.5 and 1 mol per mole of free bases present in the lactam to be purified.

13. The plant according to claim 1, further comprising:
   means for obtaining the lactam to be purified from a medium resulting from the hydrolysis of an aminonitrile after removing ammonia and treating with an ion-exchange resin.

14. The plant according to claim 13, further comprises:
   means for hydrogenating the medium resulting from the hydrolysis of the aminonitrile, and hydrogenating before removing the ammonia.

15. The plant according to claim 13, further comprising:
   means for hydrolyzing the aminonitrile in the vapor phase or in the liquid phase.

16. The plant according to claim 15, further comprising:
   means for cyclized hydrolyzing in the liquid phase, in the presence of a solvent.

17. The plant according to claim 1, wherein the lactam is caprolactam.

18. A plant according to claim 1, wherein:
   the means for adding the basic compound comprises means for adding the basic compound to the dehydration column.

* * * * *